United States Patent
Chen

(10) Patent No.: US 7,262,030 B2
(45) Date of Patent: Aug. 28, 2007

(54) MULTIPLE SEQUENCIBLE AND LIGATIBLE STRUCTURES FOR GENOMIC ANALYSIS

(75) Inventor: Xiangning Chen, Richmond, VA (US)

(73) Assignee: Virginia Commonwealth University, Richmond, WA (US)

( * ) Notice: Subject to any disclaimer, the term of this patent is extended or adjusted under 35 U.S.C. 154(b) by 152 days.

(21) Appl. No.: 10/476,970

(22) PCT Filed: May 9, 2002

(86) PCT No.: PCT/US02/14431

§ 371 (c)(1),
(2), (4) Date: Feb. 14, 2005

(87) PCT Pub. No.: WO02/090505

PCT Pub. Date: Nov. 14, 2002

(65) Prior Publication Data

US 2005/0175996 A1    Aug. 11, 2005

Related U.S. Application Data

(60) Provisional application No. 60/289,514, filed on May 9, 2001.

(51) Int. Cl.
*C12P 19/34* (2006.01)
*C12Q 1/68* (2006.01)
(52) U.S. Cl. .......................................... 435/91.2; 435/6
(58) Field of Classification Search .................... None
See application file for complete search history.

(56) References Cited

U.S. PATENT DOCUMENTS

| 6,087,485 A | 7/2000 | Brooks-Wilson et al. |
| 6,228,594 B1 | 5/2001 | Thomas et al. |

*Primary Examiner*—Young J. Kim
(74) *Attorney, Agent, or Firm*—Whitman Curtis Christofferson & Cook, PC

(57) ABSTRACT

High throughput methods and kits for single nucleotide polymorphism (SNP) genotyping are provided. The methods involve utilizing nested PCR amplification reactions which produce sequencible and ligatible structures. An outer PCR primer set amplifies the SNP, and an inner PCR primer set amplifies a portion of the DNA amplified by the outer primer set, but does not amplify the SNP itself. The inner and outer primers may reaction include non-target common domain sequences, and the inner primer common domain sequences may comprise digestion restriction endonuclease recognition sites. The design of the inner primer set allows precise tailoring of the sequencible and ligatible structures with respect to length and base composition.

20 Claims, 7 Drawing Sheets

```
agtacctgtc  agaatgagat  taccctccag  gttccaaatc  cctcagaatt
aagagccaag  ccaccttctt  cttcctccac  ctgcaccgac  tcggccaccc
gggacatcag  tgagggtggg  gagtccccg   ttgttcagtc  cgatgaggag
gaagttcagg  tggacactgc  cctggccaca  tcacacactg  acagagaggc
cactccggat  ggtggtgagg  acagcgactc  ttaaattggg  acatgggcgt
tgtctggcca  cactggaatc  cagttttggc  tgtatgcgga  attccacctg
gaaagccagg  ttgttttata  gaggttcttg  atttttacAt  aattgccaat
aatgtgtgag  aaacttaaag  aacagctaac  aataaagtgt  gaggacggta
aactgagagc  gcacagagct
```

FIGURE 3A

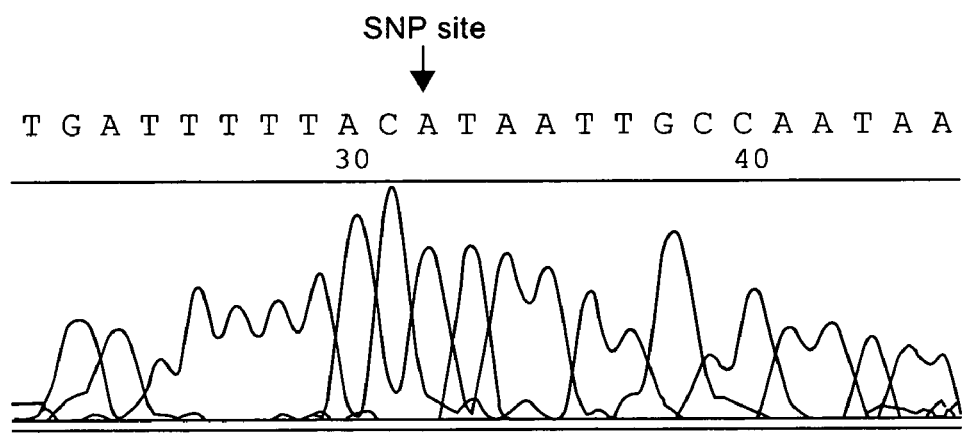

FIGURE 3B

```
atattaggca  gtgtagcaga  tgattaagaa  catggaattc  taggtgtggt
ggctcacacc  tgtaatcccc  atatgtttgg  aggccaaggc  tggaggatcg
cctgagccta  ggagttagag  accagcctgg  gcaacagagt  gagacctcgt
ctctacaaat  aattaaaaaa  ttagctggtt  gtggtggtgc  atacctgtag tccaagctcc  tccagaggct  gaggtAggag  gatcacttac  gtcagggagg
ttgaaggtgc  agtgagccac  gatcacatca  ctgcctcca   gcctgggcaa
cagagcaaga  ctctgtctct  agaaagagaa  aaagaagaac  atggaatcta
gagccagact  gggagtgctg  aaatgctagc  ttggatgtta  tctcacctct
ctgagcctca  gttccctctc  tgaaaatga   aaatgattaa  taggacctac atctttgaat  tgctttaaag  actgcattga  tacacataaa  gggtttacag
ctgtgcctgg  tatttacgta  gaagtgctgt  atataagagt
```

FIGURE 4A

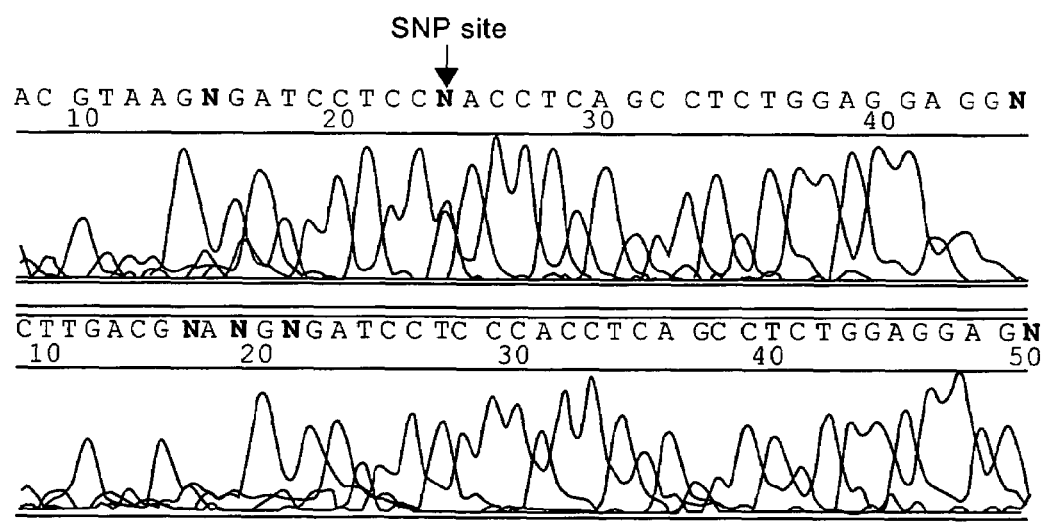

FIGURE 4B

MULTIPLE SEQUENCIBLE AND LIGATIBLE STRUCTURES FOR GENOMIC ANALYSIS

This application is a 371 of PCT/US02/14431, filed on May 9, 2002, which claims the benefit of U.S. Provisional Application Ser. No. 60/289,514, filed on May 9, 2001.

BACKGROUND OF THE INVENTION

1. Field of the Invention

The invention generally relates to single nucleotide polymorphism (SNP) genotyping. In particular, the invention provides a method for SNP genotyping based on a nested PCR design that creates structures directly suitable for both DNA sequencing and ligation reactions.

2. Background of the Invention

With the completion of the rough draft of the human genome, over 1.5 million non-redundant SNPs have been identified and mapped by the publicly funded project and the SNP consortium (Sachidanandam et al, 2001). The availability of such a large number of SNPs has prompted great interest in SNP related applications and research, such as large scale linkage, genomic association and pharmarcogenetic studies.

SNPs entered the central arena of genetics due to their abundance (Collins et al, 1997; Sachidanandam et al, 2001), stability (Sachidanandam et al, 2001) and the relative ease (Kwok 2000; Shi 2001; Syvanen 2002) with which they are genotyped. The targets of SNP genotyping are normally small pieces of DNA, ranging from 150-300 base pairs. Based on the SNP consortium report, the average SNP density in the human genome appears to be greater than 1 SNP/KB. This high density provides a tool to analyze genomic structure at very high resolution, and to establish a direct correlation between genetic coding variation and biological function. The relative stability of SNPs (compared to mini-and micro-satellite markers) in evolution makes it simpler to carry out this task.

Although SNP genotyping is generally easier than microsatellite genotyping, and despite the rapid and significant advances in SNP genotyping technology in the last few years, major issues remain unsolved. Whereas only a few years ago, the main concern was the need to have a large number of SNPs available, currently the most urgent issues are increasing throughput and decreasing cost. For example, for large scale applications as projected by Kruglyak (1999) and Long (1999), a reasonable cost would be <$0.10/genotype, or else large-scale projects will become prohibitively expensive. To fulfill the goals of understanding the genetics of complex traits and common diseases, cost-effective and higher throughput methodology in SNP genotyping is essential.

Typically, genotyping protocols have three components: target amplification, allelic discrimination and product detection and identification. They are normally executed sequentially, but can be processed in a single step reaction, depending on the means which are used for allele discrimination and signal detection. Such single step procedures are well-suited to automation, but are not necessarily effective in terms of cost and throughput.

PCR is the dominant procedure utilized for target amplification. As is widely known, a PCR can readily amplify targets present in lower copy number by a factor of $10^8$ or more. With respect to allele discrimination, all SNP genotyping technologies currently available are based on mechanisms involving one or more of the following: DNA polymerase, hybridization and DNA ligase. DNA polymerase methods include single base extension (SBE) (Armstrong, 2000; Barta 2001; Bray 2001; Cai 2001; Chen 1997; Chem 1999; Chen 1998; Chen 1997; Chen 1997; Fan 2000; Lindblad-Toh 2000; Nikiforov 1994; Pastinen 1996; Pastinen 2000; Ross, 1998; Sauer 2000; Syvanen 1999; Ye 2001), de novo sequencing including pyrosequencing (Nordstrom 2000; Ronaghi 2001), allele-specific PCR and extension (Germer 1999; Myakishev 2001; Pastinen 2000), and structure-specific cleavage (Fors 2000). Of these different forms, SBE is the most widely used and has been adapted for many different detection platforms. Hybridization is also widely used in several different forms, including dynamic hybridization (Prince 2001), and is the primary method currently used in all microarray detection formats. DNA ligase methods are based on the ability of DNA ligase to join the ends of two oligonucleotides annealed next to each other on a template (Tong 2000; Tong1999). Two oligonucleotides can be designed to anneal to both sides of a SNP site, and by detecting the formation of ligation product, the genotype of a target can be inferred (Chen 1998; Delahunty 1996; Gerry 1999; Iannone 2000).

Once a target DNA sequence has been amplified and the allelic variants discriminated, the next step in a generic genotyping protocol is to detect and identify the allele specific products. Detection mechanisms vary greatly, from simple fluorescence intensity (Armstrong 2000; Cai 2000; Chen 1998; Chen 1997; Delahunty 1996; Dubertret 2001; Fan 2000; Fergusoon 2000; Fors 2000; Germer 1999; Germer 2000; Gerry 1999; Iannone 2000; Lindblad-Toh 2000; Lindroos 2001; Marras 1999; Medintz 2001; Myakishev 2001; Nikiforov 1994; Pastinen 1997; Pastinen 2000; Prince 2001; Syvanen 1999; Ye 2001) to very precise mass (Bray 2001; Ross 1998; Sauer 2000) or electric charge (Gilles 1999; Woolley 2000) measurement. The detection mechanisms roughly fall into two categories: homogeneous and solid phase mediated detection. All homogeneous detection platforms depend on measuring fluorescence intensities and their change during and/or after reactions. One common feature among homogeneous approaches is that they do not require any separation/purification prior to signal acquisition, making them amenable to automation. Solid support techniques include flow cytometry genotyping (Armstrong 2000; Cai 2000; Ye 2001), zip-code microarrays (Fan 2000; Gerry 1999), and mass spectrometry genotyping (Bray 2001; Ross 1998; Sauer 2000). Using a solid support in the detection step may potentially increase throughput and reduce cost, but unfortunately also entails the risk of complicating protocols and compromising data quality. For example, when reaction mixtures are applied to a solid support, unintended binding of fluorescence dye to the solid surface can occur, necessitating extensive washing to minimize spurious signals.

With respect to cost, prices for genotyping technologies currently available on the market vary considerably, from $0.50-2.00/genotype. For example, the template-directed dye-terminator incorporation assay with fluorescence detection (FP-TDI) (Chen 1999) costs roughly $0.50/genotype for reagents by list price. For other methods, due to their requirement for special reagents and/or clean-up procedures, the cost is higher, e.g. MALDI-TOF mass spectrometry is about $0.75-1.00, whereas pyrosequencing approaches $2.00/genotype. No currently available technology approaches the low cost which is necessary in order to prevent large-scale projects from becoming prohibitively expensive, i.e. <$0.10/genotype.

There are currently many genotyping applications in use or under development that require a relatively large number of both SNPs and samples (e.g., both in the thousands or more), demanding both cost effective and high throughput technologies. Examples include gene mapping studies by linkage or linkage disequilibrium (Kruglyak 1999; Long 1999) for complex traits and pharmacogenetics (Riley 2000). Clearly, these applications are critical to improving our understanding of the genetics of complex traits, common diseases and drug response, and to help attain the goal of individualized medicine. However, none of the current approaches are suitable for such applications in terms of cost effectiveness coupled with high throughput potential, and SNP genotyping demands both.

SUMMARY OF THE INVENTION

The present invention provides a methodology for high-throughput SNP genotyping that is highly cost effective. This novel approach makes use of the high throughput capacity of DNA sequencers for SNP genotyping and is based on a nested PCR design that creates a series of ordered "structures" in parallel and exploits them for SNP genotyping assays. The invention thus provides novel genotyping technologies that significantly increase throughput, reduce cost and are accessible for most researchers, leading to significant improvements in genotyping technology. While typical SNP genotyping approaches currently available score <10 SNPs simultaneously, the methods of the present invention increase the number to about 50-100 with obvious advantages for throughput and cost.

The present invention provides a method of producing hybrid DNA with a single strand overhang that includes a target sequence. The steps of the method include: obtaining a first primer which hybridizes to a 5' strand of a strand of deoxyribonucleic acid (DNA), a second primer which hybridizes to a 3' strand of the strand of DNA, and a third primer which hydridizes to said 3' strand of DNA; producing by nested polymerase chain reaction (PCR) using the first primer, the second primer, and the third primer, an outer amplicon which includes a target sequence and an inner amplicon which excludes the target sequence; forming at least one of the following: a ligatable structure which includes a 3'-5' sequence which excludes the target sequence hybridized to a 5'-3' sequence which includes the target sequence, and a sequencible structure which includes a 5'-3' sequence which excludes the target sequence hybridized to a 3'-5' sequence which includes the target sequence; sequencing the sequencible structure(s) and ligating the ligatible structure(s) with a labeled oligonucleotide; and analyzing the sequencing products and ligation products with a DNA sequencer to determine the genotype of said individual. The method may form both the ligatable structure and the sequencible structure. The target sequence(s) may include a single nucleotide polymorphism.

The invention also provides a method of genotyping the deoxyribonucleic acid (DNA) of an individual by analyzing at least on target sequence in the DNA. The steps of the method include: obtaining a first primer which hybridizes to a 5' strand of a strand of said DNA, a second primer which hybridizes to a 3' strand of the strand of DNA, and a third primer which hybridizes to the 3' strand of DNA; producing by nested polymerase chain reaction (PCR) using the first primer, the second primer, and the third primer, an outer amplicon which includes said target sequence and an inner amplicon which excludes the target sequence; and forming at least one of the following: a ligatable structure which includes a 3'-5' sequence which excludes the target sequence hybridized to a 5'-3' sequence which includes the target sequence, and a sequencible structure which includes a 5'-3' sequence which excludes the target sequence hybridized to a 3'-5' sequence which includes the target sequence; sequencing the sequencible structure and ligating the ligatible structure with a labeled oligonucleotide; and analyzing the sequencing and ligation products so produced with a DNA sequencer to determine the genotype of the individual. The forming step of the method may form both the ligatible structure and the sequencible structure. The target sequence(s) may include a single nucleotide polymorphism. The sequencible structure may be sequenced by a technique such as dideoxy sequencing, pyrosequencing, and single base extension.

In a preferred embodiment, of the method, i) a plurality of target sequences is analyzed; ii) the step of forming forms an ordered series of sequencible structures; iii) the step of sequencing produces an ordered series of sequencing products of varying, non-overlapping length; and iv) the step of analyzing is carried out by electrophoresing the ordered series of sequencing products in a single channel of said DNA sequencer. In some embodiments, the step of sequencing is carried out by single base extension (SBE). In other embodiments, the step of sequencing is carried out by a dideoxy sequencing reaction utilizing a ratio of dNTPs to ddNTPs that is lower than that which is typically used in order to produce a short sequence reading.

In a preferred embodiment of the present invention, the labeled oligonucleotide is fluorescently labeled.

In one embodiment of the method, i) a plurality of target sequences is analyzed; ii) the labeled oligonucleotides are degenerate; iii) the ligation products are of varying, non-overlapping lengths; and iv) the step of analyzing is carried out by electrophoresing a plurality of ligation products in a single channel of said DNA sequencer.

The present invention also provides a method for analyzing at least one target site in a DNA molecule. The method includes the steps of: 1) amplifying the target site(s) by nested PCR; (The nested PCR is carried out using inner and outer PCR primer pairs, wherein the outer PCR primer pair forms a first PCR product which contains a target site, and the inner PCR primer pair forms a second PCR product which contains a portion of the first PCR product but does not contain the target site); 2) denaturing the first and said second PCR products to form ssDNA sequences, 3) reannealing the ss DNA sequences to form a sequencible hybrid DNA molecule and a ligatable hybrid DNA molecule, 4) performing sequencing reactions with said sequencible hybrid DNA molecule and ligation reactions with said ligatable hybrid DNA molecule, and 5) determining the characteristics of the target sequence by analyzing results obtained in the performing step. In a preferred embodiment of the method, the target site(s) may be SNP polymorphism sites. Further, the inner and outer primer pairs may comprise a sequence tag, which in turn may comprises a restriction enzyme recognition site. In some embodiments of the method, the step of amplifying may be carried out using a low concentration of primers, and may further comprising a second step of amplification using secondary primers for amplification of the sequence tags. According to the method, one or several target sites may be analyzed. The step of amplifying may be carried out in a single multiplex PCR reaction, or in multiple independent PCR reactions, and the results may be analyzed by a DNA sequencer.

The invention also provides inner and outer PCR primer pairs for the amplification of a target sequence in a DNA molecule, wherein the outer PCR primer pair forms a first PCR product which contains the target sequence, and the inner PCR primer pair forms a second PCR product which contains a portion of the first PCR product but does not contain said target sequence. The target sequence may be an SNP polymorphism site. The primer pairs may comprise a sequence tag.

The present invention also provides a kit for amplification of at least one target sequence in a DNA molecule. The kit includes inner and outer PCR primer pairs for the amplification of the target sequence. The outer primer pair amplifies a portion of the DNA molecule which includes the target sequence, and the inner primer pair amplifies part of the same portion of the DNA molecule that is amplified by the outer primer pair, but excludes the target sequence. The inner and outer PCR primer pairs may comprise sequence tags. The kit may further comprise secondary primers for the amplification of the sequence tags.

The present invention also provides a dideoxy DNA sequencing kit for producing short chain termination fragments. The kit includes dNTPs and ddNTPs which are present in a low dNTP:ddNTP ratio.

BRIEF DESCRIPTION OF THE DRAWINGS

FIGS. 3A and B. A. Depiction of nested PCR primer design. The sequence (SEQ ID NO. 1) represents 393 nucleotides from human chromosome 6. Nucleotides corresponding to primer pairs are shaded with gray, and arrows indicate primer orientation. Arrow indicates site of polymorphism. The sequence which was generated by ABI 377 sequencer is shown in italics, and is also depicted in FIG. 3B (SEQ ID NO. 2). The sample is a A/A homozygote.

FIGS. 4A and B. A. Depiction of nested PCR primer design. The sequence (SEQ ID NO. 3) represents 494 nucleotides from human chromosome 6. Nucleotides corresponding to primer pairs are shaded with gray, and arrows indicate primer orientation. Arrow indicates site of polymorphism. The sequence which was generated by ABI 377 sequencer is shown in italics, and is also depicted in FIG. 4B (SEQ liD NO. 4). Two samples were shown in FIG. 4B. The upper panel was a heterozygote (C/T), at base position 24, as pointed by the arrow, both bases C and T) were identified. The lower panel was a homozygote (T/T), at the indicated position only the T base was identified. The example demonstrated that a single nucleotide polymorphism (SNP) could be identified by sequencing from the sequencible structure formed from the nPCR design.

DETAILED DESCRIPTION OF THE PREFERRED EMBODIMENTS OF THE INVENTION

The present invention provides methods of high-throughput SNP genotyping that are highly cost-effective. The methods utilize the high-throughput capability of ubiquitous and readily accessible DNA sequencers in order to carry out the SNP analysis. This is possible due to the experimental design of the methods, which are based on nested PCR reactions. In a preferred embodiment, the target sites which are analyzed are SNP polymorphism sites.

However, those of skill in the art will recognize that other target sites may also be analyzed by the methods of the present invention. For example, short insertions and deletions, and closely spaced multiple SNPs can be identified by the multiple target sequencing approaches disclosed herein.

As is well-known to those of skill in the art, nested PCR is a PCR amplification method that "nests" one PCR reaction within another. Two sets of primers are used: "outer" primers amplify a portion of a DNA strand, and "inner" primers amplify a smaller portion of the same DNA that is located within the larger, outer portion. Thus, two PCR products (amplicons) are produced. One amplicon is smaller than the other and contains a "subset" of the bases contained in the larger, outer amplicon.

Figure 1:
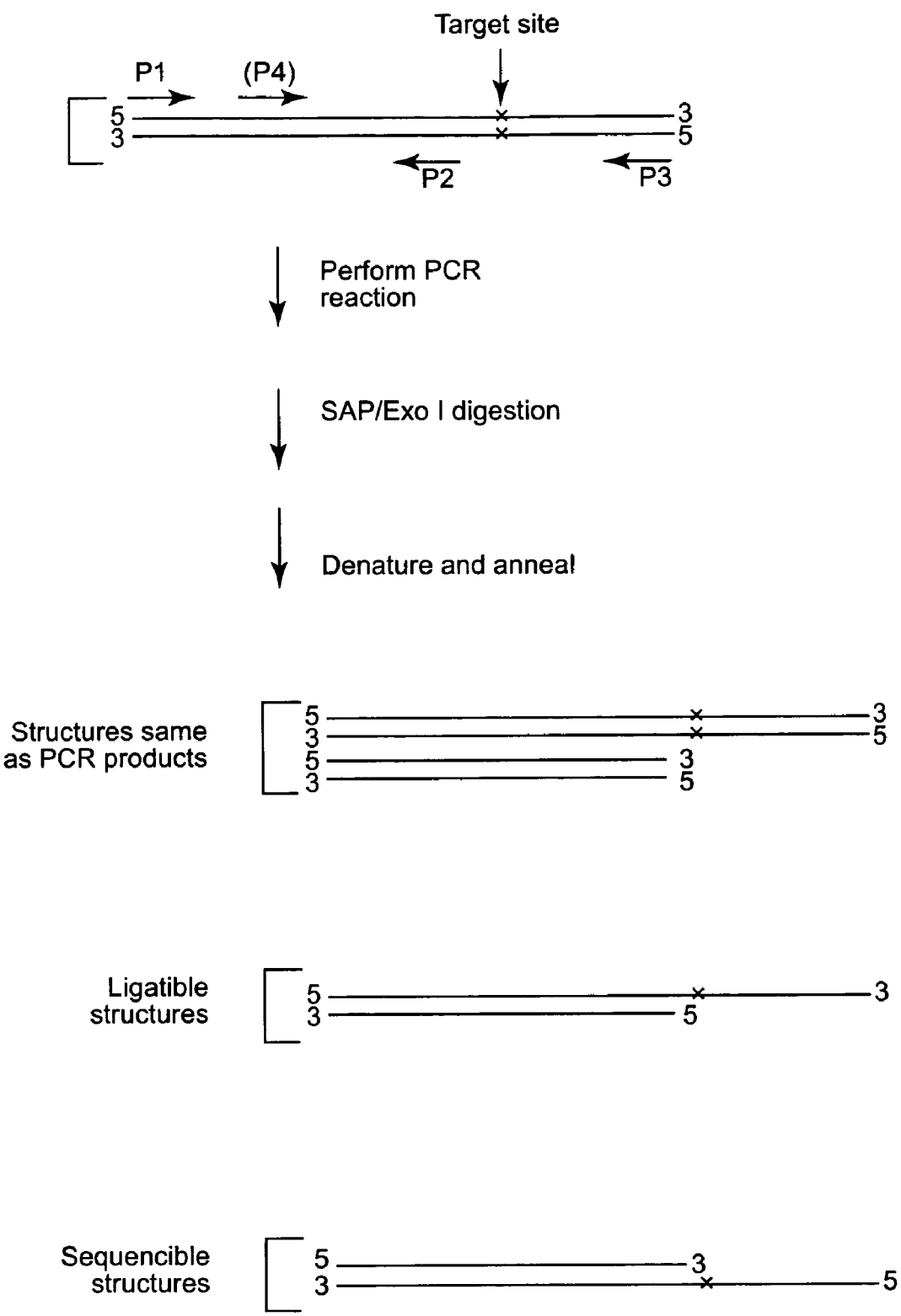
FIG. 1. A schematic drawing illustrates a nested PCR design that would create both a sequencible and a ligatible structure. The reaction uses two primer sets (inner and outer). P1, forward outer and forward inner primer; P2, reverse inner primer; P3, reverse outer primer. When this design is multiplexed, multiple sequencible and a ligatible structures are formed. These structures can be used for genotyping reactions.

In the practice of the present invention, a new design for nested PCR is used. Primers are designed so that the outer amplicon includes a target site (e.g. an SNP polymorphism site) and the inner amplicon excludes the target site. The purpose of the inner PCR in the nested reaction is to synthesize a DNA fragment whose size and position relative to the outer PCR can be precisely controlled. This design concept is illustrated in FIG. 1. As can be seen, in FIG. 1, the inner primer set is composed of primers P1 and P2, and the outer primer set is composed of primers P1 and P3. (In this example, Primer P1 is utilized in both primer sets.) The P1-P3 outer primer set flanks the indicated target site whereas the P1-P2 inner primer pair does not. PCR amplification of the DNA with these primers will produce two amplicons. The larger of the two is the outer amplicon formed by amplification with the P1-P3 pair; this amplicon includes the target site. The smaller of the two amplicons, the inner amplicon, contains base pairs which lie within the bounds of the larger outer amplicon (i.e. is "nested" within the larger amplicon), but does not contain the target site. The ultimate product of the PCR reaction is double strand DNA of two lengths, only one of which (the longer) contains the target site, and the shorter of which contains a subset of the bases contained in the longer strand.

In a preferred embodiment of the invention, the same primer functions as both the outer and inner forward primer. However, those of skill in the art will recognize that this need not be the case. With reference to FIG. 1, a distinct forward inner primer ("P4", shown in parentheses) might be designed to anneal between P1 and P2 and in the orientation of primer P1. Because the shorter amplicon contains bases which are identical to a portion of the longer amplicon, when the ds strands are denatured and allowed to reanneal, some (approximately 50%) of the shorter single strand DNA of the inner amplicon will hybridize with matching portions of the single strand DNA of the outer amplicon. This cross hybridization between the two amplicons creates two different inner-outer "hybrid" structures as depicted in FIG. 1. In one of the two structures, the "ligatible structure" of FIG. 1, a 3' overhang will be present, the bases of which originated from the outer amplicon and contain the target site. This structure can be used, for example, for ligation based applications. By "ligation based applications" we mean the smaller amplicon is one of the two or more pieces of DNA that are joined together by a DNA/RNA ligase. In the other structure, the "sequencible structure" of FIG. 1, a 5' overhang will be present, the bases of which originated from the outer amplicon and also contain the target site. This second type of structure will be directly amenable to sequencing applications. By "sequencing applications" we mean that the smaller amplicon acts as a sequencing primer to sequence the DNA downstream from it. The sequencing can be only one base in length (i.e. SBE) or in the tens or in the hundreds of bases. Thus, in a single nested PCR reaction followed by denaturation and annealing, it is possible to generate both sequencible and ligatible structures. Of course, some (approximately 50%) of the single strand DNA will renature to form the original ds PCR products ("structures same as products" in FIG. 1).

Years of improvement in primer design and thermocycling conditions have increased the success rate for single target PCR reactions to greater than 90%. However, multiplex reactions such as those in a nPCR reaction, have a much lower success rate and extensive optimization is typically required, usually because it is very difficult to obtain amplified products in equal amounts. The usual solution is to increase the primer concentration for the weakly amplified target(s). This suggests that it is annealing efficiency that is responsible for the unequal amplification. In U.S. Pat. No. 5,882,856 to Shuber, the complete contents of which is herein incorporated by reference, an alternative solution is proposed in which all primers utilized have two domains, one which is target specific as in regular PCR designs, and one which is a "common domain". For a set of PCR primers to be multiplexed, two common domains are utilized. A first common domain is a sequence shared by all forward primers and is attached at the 5' end of the target specific domain. A second common domain sequence is shared by all reverse primers and is attached at the 5' end of the target specific domain. The common domain facilitates annealing of different primer sets because the common domain has a higher annealing temperature than the target specific domain.

In the practice of the present invention, common sequence domains or "sequence tags" as taught by Shuber may be utilized for both inner and/or outer PCR primers. The common sequence tag for the outer PCR primers would help in multiplexing PCR so that amplification would result in the production of equal amounts of product. The common sequence tag for the inner primers also serves to even the levels of PCR products, and in addition may provide restriction sites that can be used to generate precise fragment ends for genotyping reactions such as sequencing and/or ligation reactions. The combination of incorporating special restriction enzyme recognition sequences in such a sequence tag, and the deliberate positioning of the inner PCR primers make it possible to precisely tailor the resulting PCR products for any of a variety of purposes, including but not limited to primer extension, sequencing, ligation, pyrosequencing, structure specific cleavage, and other genotyping reactions.

Those of skill in the art will recognize that placement of the P2 primer can be anywhere between the target site and the other primer of the inner primer pair, so long as a useful PCR product is produced by PCR amplification of the inner primer pair, and the target site itself is not amplified. The positioning of the P2 primer relative to the target SNP may vary depending on the mechanism of the genotyping reactions. For example, for SBE reactions, the end of the primer should be immediately 5' to the SNP site. For Multi-Target Sequencing (NulTarSeq) reactions, there may be a gap between the end and the target SNP site. In a preferred embodiment, for MulTarSeq reactions the gap may be from about 1 to 50 bases, or more preferably from about 5 to about 20 bases, and most preferably from about 10 to about 15 bases. Further, as described above, the desired length of the final product from the amplification of PCR primers containing common sequence tags may also be determined by the presence of a restriction enzyme cleavage site within the tag.

In yet another embodiment of the present invention, the amplification reactions may be carried out in a step-wise fashion using primary and secondary primers. In this embodiment, a single PCR is divided into two sequential reactions, the first of which uses the primary primer set and the second of which uses the secondary primer set. The primary primers may be designed to have two domains (target specific and common) as described above. The secondary primer set contains only the common tails from the primary primers.

For the first reaction, the primary primers are used in only limited but equal amounts, e.g. about 1-5% of the amount for a regular PCR i.e. about 0.1 to about 100 nM. The rationale is that by limiting the amount of primers for each set multiplexed in the reaction, the system is forced to produce limited but equal amounts of products for all amplicons. When the more robust primers are used up (because of the limited amount available) the system will work with the less efficient primers. The purpose of the primary PCR is to amplify enough templates from the genomic DNA to carry out the secondary PCR. Since all primary primers have limited but equal amounts, this forces the primary PCR to produce limited but near equal amounts of templates for the secondary PCR. For the secondary PCR, the secondary primers, consisting of only one set for all primary amplicons, is used. In essence this secondary reaction is a single PCR that amplifies multiple templates. The net result of this two-step PCR process is to compensate for differences in efficiency across PCR reactions.

The purpose of the inner PCR in the nested reaction is to synthesize a DNA fragment whose size and position relative to the outer PCR can be precisely controlled. By altering the position of the P2 primer relative to P1, and by optionally including sequence tags with restriction sites, it is possible to design longer or shorter PCR fragments. The synthesized fragments can then be used in any of a variety of genotyping reactions, including but not limited to primer extension, sequencing, ligation, pyrosequencing, structure specific cleavage, and the like.

For example, the sequencible structure fragments may be used as extension primers in SBE and MulTarSeq reactions. The direct production of sequencible structures by the methods of the present invention thus permits investigators to take advantage of the ready availability of DNA sequencers for the purposes of genotyping. Relatively long primers can be synthesized in this manner in a feasible and much more cost effective way than, as is typically done, by chemical synthesis. For example, the length of such a fragment can range from about 35 to about 1000 bps, and is preferably in the range of about 50 to about 650 bps. To use a standard sequencing reaction to determine the sequences surrounding a polymorphic site, it is simply necessary to add an appropriate sequencing mixture without using any sequencing primer, because the sequencible structure provides the free 3' end for the sequence reaction.

Those of skill in the art will recognize that several methods of sequencing are well established, and that new sequencing methodologies are continually being developed. In the practice of the present invention, any suitable method of sequencing may be utilized. Examples of such methods include but are not limited to Sanger (dideoxy)-based sequencing methods and pyrosequencing.

Figure 2A:
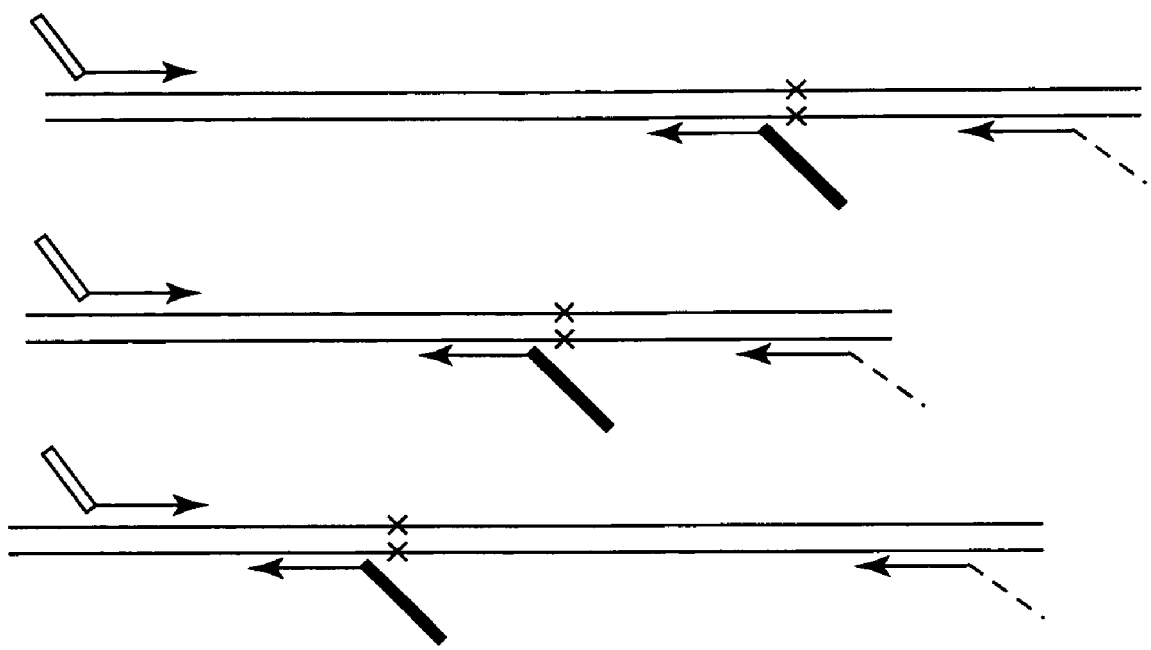
FIGS. 2A and B. A, a multiplex PCR scheme that amplifies three target sites. Two primer sets (inner and outer) are used for the amplification of each target site. The target sites are represented by "x". All primers contain two domains, a common domain and a target specific domain. The target specific domains, indicated by arrows, have sequences unique to the targets, whereas the common domains are not target specific. ▯= common domain of forward inner and forward outer primers; ▮= common domain of inner reverse primers; --- = common domain of reverse outer primers. B, close-up view of common domain of inner primer (SEQ ID NO: 8) shows restriction sites incorporated into the sequence of the domain.
Figure 2B:
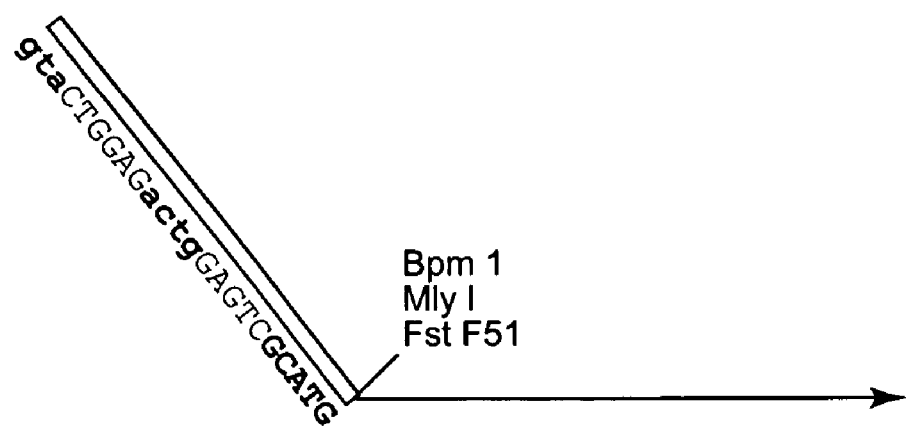

The procedure illustrated in FIG. 1 amplifies a single target and relies on multiplex PCR amplification since more than one pair of primers is used in a single reaction. However, those of skill in the art will recognize that in many cases it will be desirable to amplify more than one target site at a time. In this case, the design of the inner primer pairs for each target site may be such that an ordered series of PCR products of varying lengths is produced, i.e. the sequencible structure formed for each target site differs in length from the sequencible structures formed for each of the other target sites. (See FIG. 2A). For example, an ordered series of sequencible structures from about 50 to about 500 bps in length can be designed, thus adding an additional distinguishing feature to each of the amplified target sites. Because of this feature, multiple sets of PCR products can be sequenced in a single reaction providing that the length of sequencing is limited so that their chain termination fragments do not overlap in a sequencing gel. This would allow the sequencing of multiple targets in a single reaction and analysis in a single channel (e.g. a lane or capillary).

Those of skill in the art will recognize that several ways exist to control the length of reading for sequencing reactions. For example, the length of reading can be adjusted by changing the ratio of ddNTP/dNTP in the reaction mixture. For standard Sanger sequencing reactions, the ratio is typically about 1:100, a ratio intended to promote relatively long reads (e.g. about 600-800 bps). Those of skill in the art will recognize that, by systematically altering and testing the ratio, it is possible to find the optimal reading length for a given application. For most SNP genotyping purposes, a read of from about 1 to about 50, and preferably from about 1 to about 25 bases would be sufficient, requiring a low ddNTP/dNTP ratio of preferably in the range of about 1:0 to about 1:10, and more preferably about 1:0 to about 1:5. For other applications, the optimal length can be attained by adjusting the ratio, i.e. the ratio may be optimized by methods which are well known to those of skill in the art in order to achieve the desired sequence read length. Precise control of the read allows very high level multiplexes to be carried out (e.g. 100 to 200×). In order to carry out the practice of the present invention, primer design involving placement of the primer and the optional addition of a sequence tag must be carried out.

Further, those of skill in the art will recognize that other factors influence primer design and must be taken into account as well. For example, the exact sequence of bases will influence the strength of the hybridization of the primer with its cognate DNA (the sequences of based to which it binds during PCR) and thus must be taken into account when planning PCR amplification protocols; the possibility of primer-dimer formation is taken into account, as is the potential for the formation of secondary structure, etc. Those of skill in the art are well acquainted with such issues and numerous resources exist to aid the skilled practitioner in these various aspects of primer design.

As discussed above, the common domains of the inner primers may be designed to include restriction enzyme recognition sites. The restriction enzymes preferred are those that cleave DNA strands downstream from their recognition sites and generate blunt ends products. For sequencing applications restriction enzymes that cleave DNA downstream and generate 3' overhangs can also be used. For ligation applications restriction enzymes that cleave DNA downstream and generate 5' overhangs can also be used. Examples of such sites include but are not limited to these enzymes: Mly I, Fst F51, Bpm I, Eco57I, Bsg I, Eci I, Bst71 I, Alw26 I, Ksp62 I, BceA I, etc. The other nucleotides in the sequence of a common domain inner primer are selected to balance the melting temperature with that of the common domain of the outer primers. With respect to the design of common domain sequences for outer primers (i.e. those which do not contain restriction sites), the sequences are selected so that so it will match the melting temperature of the common domain of the inner primer.

In general, the generation of the sequencible and ligatible structures of the present invention will be carried out as follows: a PCR amplification reaction is carried out, followed by a restriction with a suitable restriction enzyme if a restriction site was incorporated into a common sequence tag of the inner primers. This is followed by treatment to "clean up" the reaction e.g. with shrimp alkaline phosphatase (SAP) and exonuclease I (Exo I) to degrade excess PCR primers and dNTP left over from the PCR reaction, and to remove the overhanging ends of restriction digestion. (Alternatively, filtration via sephadex gel may also be employed.) After SAP/Exo I digestion, a high temperature denature step is performed. This denature step serves two purposes: one is to inactivate both SAP, Exo I and the restriction enzyme; the other is to completely denature double stranded DNA. During the cooling process that follows, the four single stranded DNA fragments from the two PCR products will form four kinds of structure. Two of them are the exactly same as the PCR products and are both blunt ended. Two new structures formed between the complementary strands of the large and small PCR products, one of them with a 5' end single stranded, the other one with a 3' end single stranded. The one with a 5' end single stranded provides a free 3' end for sequencing reaction/primer extension and for ligation, and is referred to as a "sequencible structure". The one with single stranded 3' end provides a free 5' end for ligation, and is referred to as a "ligatible structure". These four structures will have equal concentrations if the quantity of the two PCR products is equal. In this case, the sequencible and ligatible structures will represent about 50% of the reannealed products. This amount is sufficient for both sequencing/primer extension and ligation reactions to make new products.

In some embodiments of the present invention, a single target site is analyzed by the methods of the present invention, and the PCR step is carried out by multiplex PCR, i.e. amplification with both the inner and outer primers is carried out in the same reaction. However, those of skill in the art will recognize that two separate PCR reactions may also be carried out, i.e. the inner and outer PCR reactions are carried out separately. In this case, the PCR products from the two reactions may be combined later at some point prior to the renaturation step so that the single strands can reanneal.

Similarly, in other embodiments of the present invention, it may be desirable to PCR amplify more than one target site at a time. In some cases, this may be carried out by a multiplex PCR reaction in which inner and outer primers for all target sites of interest are amplified simultaneously in a single reaction. Alternatively, one or more sites may be amplified together, or each site may be amplified alone, either in a single reaction with both inner and outer primers, or in two reactions, one for the inner and one for the outer primers as described above. Any combination of PCR amplification reactions may be utilized in the practice of the present invention, so long as the procedure results in the production of suitable sequencible and/or ligatible structures.

In a preferred embodiment, the present invention provides methods which ultimately utilize DNA sequencers or the like to detect the products formed from sequencible and/or ligatible structures created by the present methods. Those of skill in the art will recognize that many suitable techniques exist by which the sequencible products can be produced for analysis by a DNA sequencer. Examples include but are not limited to Sanger-type sequencing reactions, single base extension (SBE), and pyrosequencing. Ligatible structures may be analyzed directly on a DNA sequencer after a labeled oligonucleotide (e.g. fluorescently labeled) is joined to the 5' phosphate of the ligatible structure via a ligation reaction.

Those of skill in the art are well acquainted with Sanger-type sequencing reactions, which are based on the interruption of enzymatic extension of the DNA chain at the 3' hydroxyl via incorporation of 2'-3'-dideoxy analogs. Four sets (one for each dideoxy analog) of such chain-terminated fragments of differing lengths are generated and "read" (detected) by a DNA sequencer to yield a sequence. Typically, the fragments are labeled with radioactivity or fluorescent tags for detection.

Single base extension is essentially a sequencing reaction, the difference being that SBE uses only dye-terminators, resulting in the extension of the primer by only a single base. As described above, in the practice of the present invention, the length and position of the extension primer relative to the polymorphic site may be controlled so that it is possible to create a primer which anneals immediately upstream of a polymorphic site. Then, in a regular SBE reaction, the polymorphic base can be determined by identifying which base(s) is incorporated into the primer. If several target sites are to be analyzed, a set of primers can be designed which, upon amplification of the targeted DNA, produce an ordered set of such sequencible structures of varying, non-overlapping lengths. When such structures are extended by dye-labeled ddNTPs, an ordered series of SBE products of varying, non-overlapping lengths is produced. In the proposed nested PCR design, because extension primers from about 50 to over 500 bases can be obtained, it is possible to separate these SBE products in a sequencing gel/capillary. A regular sequencing gel can sequence about 500-800 bases. Therefore, over 100 SNPs can be analyzed in a single channel by loading their corresponding SBE products in one lane/capillary when the extension primers are designed to be positioned, for example, every 4-5 bases apart for a full range of 500-600 bases.

In order to successfully carry out SBE reactions, the ends of the primers must be precise, i.e. it is necessary to control precisely where the inner amplicon ends. The use of Taq DNA polymerase may in some cases be disadvantageous due to its known extendase activity which interferes with such precision. Those of skill in the art will recognize that a variety of means are available to overcome such a problem.

For example, the use of high fidelity polymerases may be employed. Pfu DNA polymerase is a well characterized DNA polymerase that has been shown to have high fidelity of replication (Cline 1996). It is known that Pfu DNA polymerase does not add extra A's at the 3' end (Cline 1996; Hu 1993). Based on a study by Cline et al (Cline 1996) the use of Pfu DNA polymerase gives precise ends of inner PCR products.

A second alternative is to use ribonucleotides and/or abasic analogs in the inner primer to control DNA polymerases' end point. Some DNA polymerases do not have reverse transcriptase activity, Pfu and Vent polymerases are examples (Perler 1996). These enzymes can not incorporate any nucleotide when they encounter a ribonucleotide base in a template. Coljee et al recently reported a strategy to create precise overhang at the ends of PCR products by using ribonucleotides (Coljee 2000). The strategy inspired us to use same mechanism to control the ends of inner PCR products. Thus, inner primers may be designed to overlap the target SNP site, at the SNP site, instead of using regular deoxyribonucleotide, a ribonucleotide is used. DNA polymerases can use a chimeric oligonucleotide as primer efficiently (Gal 2000; Stump 1999), so the use of chimeric primers would not compromise PCR efficiency. When the complementary strands are synthesized, the DNA polymerases will stop one base before the ribonucleotide base in the chimeric inner primers, creating very accurate and precise ends for SBE. It is also possible to create chimeric primers containing several ribonucleotide bases to create several base overhang for the purpose of ligation (Coljee 2000). Similarly, a nucleotide analog that does not contain the base, the abasic analog, has similar effects on DNA polymerase (Gal 2000; Gal 1999) and may be used.

Yet another alternative is to use restriction enzymes to produce precise 3' ends for sequencible structures. There are some restriction enzymes that cleave DNA strands downstream from their recognition sites, e.g. KSP632 I, Alw26 I, and Bst71 I. As discussed above, to take advantage of these features, a common domain (sequence tag) may be added to the 5' end of the inner PCR primers. The common domains contain restriction enzyme sites which can be positioned so that the 3' extending ends are located just before the polymorphic sites after the tail is cleaved off. The use of a common domain for inner primers could also help to even the amounts among different amplicons when multiplexed.

Pyrosequencing is a unique technique that incorporates a sequencing reaction and real time detection together. Since, as in a regular sequencing reaction, pyrosequencing uses DNA polymerase, the free 3' termini in the sequencible structures can function as extension primers. Since pyrosequencing is a real time system, it is not amenable to the analysis of multiplex reactions. There would thus be no need to use a common tail for the inner PCR primers. The primers for a reaction whose products are destined for analysis by pyrosequencing are designed to accommodate the needs of pyrosequencing, preferably from about 5 to about 8 bases upstream of the target polymorphic site.

The ligatible structures produced by the methods of the present invention have a free 5' phosphate. If a common tag is included in the design, when the common tag is removed from the inner PCR products, restriction enzyme digestion leaves the 5' phosphate on the ligatible structure. To make such a ligation site at a polymorphic site, the cleavage site of restriction enzymes used in the inner PCR primer must be immediately down stream of the polymorphic site on the complementary strand. Those of skill in the art will recognize that, because all of these restriction enzymes produce a 5' over hanging strand, a suitable design of restriction site for ligation assay would not be suitable for SBE reaction, but could be used for MulTarSeq reaction. Further, one advantage of the use of ligation to score a polymorphism is that it can be combined directly with the PCR reaction; resulting in a closed tube assay.

To be detected by a DNA sequencer, DNA fragments have to be labeled with fluorescence dyes. In the present nested PCR design, the PCR products are not labeled with any fluorescence dye. Thus, the ligatible structures can be detected only if they are ligated to a labeled oligonucleotide, e.g. one that bears a fluorescent label. To be ligated onto a ligatible structure created by restriction enzyme digestion and subsequently detected by a DNA sequencer, an oligonucleotide would have a 3' OH group and 5' fluorescence labeling. Current DNA sequencers typically analyze fluorescence with a spectrum between 510-610 nm. Those of skill in the art will recognize that there are many fluorescence dyes available in this range. For example, the BODIPY series of fluorescent dyes have been shown to minimize emission overlaps between dyes (Metzker 1996). Examples of other dyes which may be utilized to carry out this aspect of the invention include but are not limited to FAM, fluorescein, R110, R6G, TAMRA, ROX, Texas red, etc.

If only a single locus is of interest is to be analyzed, locus-specific fluorescence-labeled oligos may be utilized. However, in order to carry out high level multiplex reactions, sets of degenerate, fluorescence-labeled oligos are desirable. For example, in order to make ligatible structures suitable for high throughput genotyping assays, a common set of four fluorescence dye labeled degenerate oligonucleotides may be utilized. The degeneration of the oligonucleotides is to make them reusable for all potential assays. If an oligonucleotide with a specific sequence is used, it would only work for one particular target.

Several important issues must be taken into consideration regarding the design of the degenerate oligonucleotides. One is the length of the oligonucleotide, which effects both ligation efficiency and the concentration of a specific sequence in the degenerate oligo population). For example, for a 6-7 mer oligo containing 5-6 degenerate bases, any given sequence would have a concentration of $1/4^3$-$1/4^4$ (i.e. $1/1024$-$1/4096$). If the total concentration for a 7-mer degenerated oligo used in ligation is 1 µM, the effective concentration for any giving sequence would be greater than 0.2 nM, a concentration at least 100 fold above the detection limit of sequencing gel/capillary. Those of skill in the art will recognize that the optimal length of the degenerated oligo and its concentration may vary from experiment to experiment, depending on the level of degeneracy and multiplex used in the reaction. However, the oligo will generally be in the range of about 5- about 20 bps in length with from about 4 to about 19 degenerate bases, and more preferably in the range of about 6 to about 8 bps in length with about 4 to about 6 degenerate bases.

Another consideration is the melting temperature for the degenerated oligonucleotide. As is well known to those of skill in the art, the Tm will vary depending on factors such as the GC content, the length of the oligo, and the like. For example, increasing the GC content and/or the length of an oligo increases its Tm. Increasing the length of oligonucleotide will increase $T_m$, but would decrease the effective concentration for a specific sequence. In addition, other factors such as the ionic strength of the ligation buffer also affect $T_m$ significantly. Other considerations involved in oligo design which are well-known to those of skill in the art include the number and position of bases which are degenerated. The number of degenerated bases will have a significant impact on the effective concentration and $T_m$. For example, if 5 degenerated bases are used within a 7 mer, 16 oligos must be synthesized, but if 6 degenerated bases are used, only 4 oligos are necessary. While one specified position must match the polymorphic site if multiple specified positions are used, the position does not necessarily have to be the last one on the 3' end. Further, the position of the ligation site relative to SNP site (the 5' end or the 3' end) may also be altered to optimize a given experiment. Previous studies (Tong 2000; Tong 1999) have suggested that DNA ligase exhibits better allelic discrimination when the ligation site is on the 3' end.) Those of skill in the art will recognize that many tools exist and are well-known to the skilled practitioner for optimizing such parameters, thereby facilitating the design of suitable oligos. (See, for example, Delahunty1996, Tong 2000; Tong 1999). Examples include but are not limited to various computer soft ware packages such as DNA Star, Oligo, Primer Express, etc.

Other factors which may be considered include the type and concentration of ligase to be employed. For example, a 6-7 mer oligo with a moderate GC content should exhibit a melting temperature between 30-40° C., a Tm sufficient to perform a cyclic ligation assay. The use of thermal stable DNA ligase would provide an opportunity for multiple cycling of a ligation assay at this temperature, which would compensate for lowered efficiency of the reaction.

Those of skill in the art will recognize that a plethora of protocol references, kits, etc. are readily available to facilitate carrying out such manipulations of the DNA. The precise nature of the protocols which are used is not a central feature of the present invention, and any of many suitable means for carrying out the various steps of PCR amplification and detection and analysis of the amplicons may be utilized in the practice of the present invention.

Those of skill in the art will recognize that a variety of additional well-known techniques may be reliably utilized in the practice of the present invention, examples of which include but are not limited to: mass spectroscopy, ELISA techniques, fluorescence intensity/energy transfer/polarization, various micro assays (e.g. DNA/RNA arrays), microfluidic devices, and magnetic/color-coded micro beads.

In a preferred embodiment of the present invention, the method of detection is capillary electrophoresis. The demand from the human genome project greatly stimulated technology development in DNA sequencing and, in return, improvements in DNA sequencing greatly speeded up the human genome project. As a result, capillary DNA sequencers became widely available to researchers in both academe and industry. Capillary DNA sequencers are highly sensitive and automated detection systems. They also have a relatively broad detection range, covering at least three orders of magnitude. Their analytical power is better than most signal detection systems currently used for SNP genotyping. Capillary DNA sequencing systems have been proven to deliver ultra high throughput in many DNA sequencing centers around the world.

Capillary electrophoresis has been used in DNA polymorphism analysis (Barta, 2001; Medintz 2001). Most of these studies exploited the sensitivity and speed of separation. Lindblad-Toh et al (2000) used a DNA sequencer to increase throughput. In this study, the authors chemically synthesized oligonucleotides from 18-50 bases as extension primers and succeeded in scoring 14 SNPs in one lane (The size difference between primers was 4 bases, there were a few sets of oligos of the same length but of different sequences that were used to score two different SNPs by different colors). This study essentially proved that DNA sequencers had the potential for high capacity SNP scoring using the SBE format, and the length of primers was the limiting factor for throughput.

The wide availability, high detection sensitivity, high throughput capacity and automation readiness of capillary DNA sequencers call for high capacity applications, and SNP genotyping is one of such applications. If these two are united, considerable advances in cost and throughput would be achieved. Many did not consider DNA sequencers for high throughput SNP scoring mainly because it was not cost-effective. DNA sequencers separate DNA fragments by sizes and colors. In order to separate genotyping products by a sequencer, the products must be different in sizes and or colors. To separate two SBE products, for example, SBE primers must be different in length or the extended bases must be different in color. Otherwise, the two products of same length and same colors would not be distinguished. While it is reasonable to chemically synthesize primers of 15-40 bases, this size range gives only limited multiplex capacity (Lindblad-Toh 2000)). To chemically synthesize primers longer than 50 bases is not economical, especially in high throughput settings. But a sequencer can separate DNA fragments up to 600-800 bases. In the practice of the present invention as described above, SBE products can be arranged to be 5 bases apart for 600-800 bases, allowing the loading over 100 SBE products in one lane. Multiplexing at this level makes it reasonable to use sequencers for SNP scoring. Furthermore, practical protocols for using DNA sequencers are well-established and many handling and procedures involved have been automated and are readily available for large scale applications.

The following examples are intended to be illustrative in nature and are not intended to be limit the scope of the invention in any way.

EXAMPLES

Example 1

Formation of Sequencible Structures

Sets of nPCR primers were designed as described to amplify DNA fragments from six markers of human chromosome 6 and individual nPCR was performed using Taq-Gold DNA polymerases. Clean-up digestion was carried out using shrimp alkaline phosphatase and *E. coli* exonuclease I (37° C. 1 hour) After the clean-up digestion, a high temperature denaturing (95° C. for 15 min.) was performed and the samples were allowed to cool to room temperature. A sequencing reaction was performed using standard sequencing kits but without sequencing primers. Sequencing reactions were performed either: 1) under standard cyclic sequencing program: 25 cycles of 96° C. for 1 min., 50° C. for 15 sec. and 60° C. for 4 min; or 2) using this condition: 25 cycles of 96° C. for 1 min., 80° C. for 4 min. The purpose of these experiments was to test whether a sequencible structure formed after denaturing and reannealing of the outer and inner PCR products together. If we obtained sequences and the sequences matched the inner PCR primer position, this would confirm that sequencible structures did form as expected.

The results from experiments with two of the six markers are shown in FIGS. 3A and B and FIGS. 4A and B. These figures show the results obtained with the second sequencing reaction protocol. FIGS. 3A and 4A show PCR primer positions and orientations, and the expected sequences. Note that in FIG. 4, the inner PCR primer is designed in the same orientation as forward, so the sequence reading from a sequencing reaction would be reverse complementary to the sequences highlighted with italics. FIGS. 3B and 4B show sequencing reads from the ABI 377 sequencer analysis software.

For the 6 markers tested, we obtained sequences for five, and all of these sequences matched the expected sequences exactly. Full length sequence reads (from the ends of inner PCR products to the ends of outer PCR products) were obtained when the standard cyclic sequencing conditions were used (data not shown). Much shorter sequence readings (30-50bases) were obtained when the extension temperature was changed to 80° C. (as in FIGS. 3 and 4). For 4 of the 5 makers that produced sequences the sequence started right after the inner primers, one started 3 bases away from the end of the primer. For both sequencing conditions, the starting positions of sequencing were the same.

Example 2

Creating Sequencible Structures with Products from Extendase-Free Pfu DNA Polymerases that can be Used for SBE Genotyping Reactions The variations of starting position of the obtained sequences (Example 1) suggested that the positioning of inner PCR primers alone may not be sufficient to obtain sequencible structures with precise extending ends. An alternative is the use of extendase-free DNA polymerases that do not add the 3' A base at the ends of PCR products. Thus, experiments were carried out using Pfu DNA polymerases which have been reported for lacking the extendase activity (10, 28). Inner PCR primers were designed so that their products would be positioned right before the polymorphic site if the products formed sequencible structures. Inner and outer PCR reactions were performed separately using Pfu DNA polymerases and the products wqere pooled together to form the sequencible structures. Then a SBE reaction was performed using SNaPshot kit from Applied BioSystems. SBE reactions were purified and analyzed by ABI 377 DNA sequencer using GeneScan.

Figure 5:
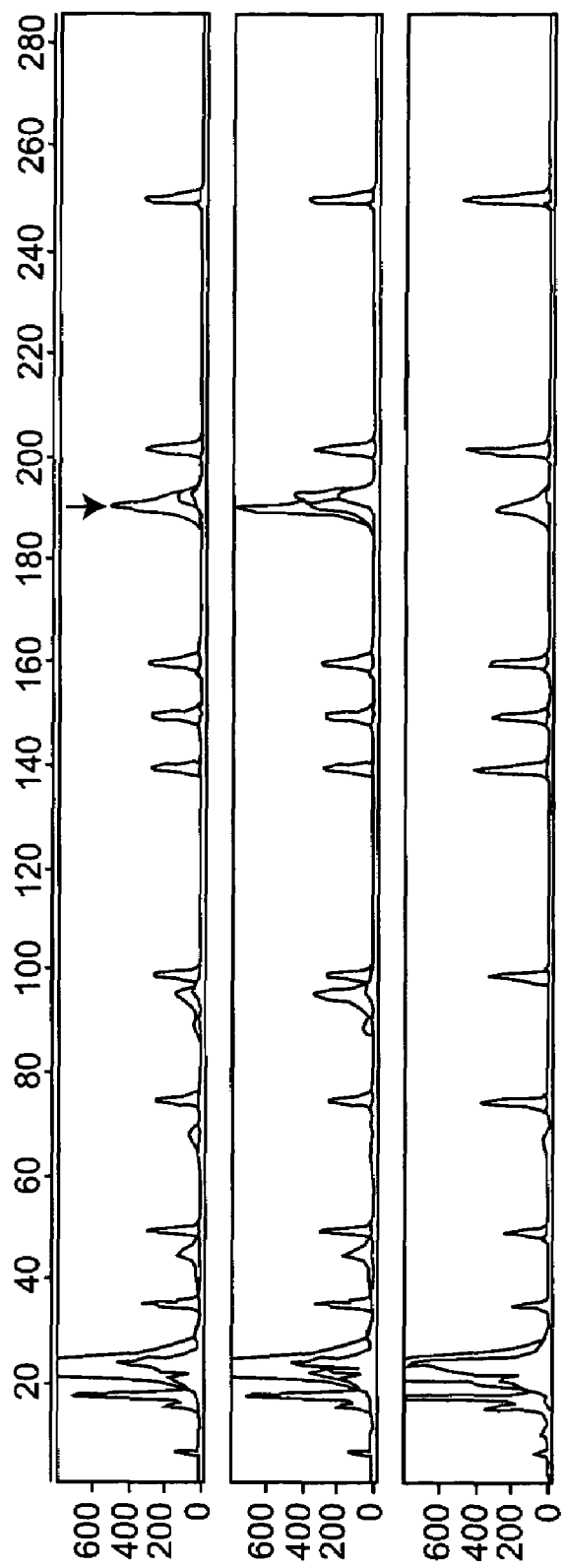
FIG. 5. SBE genotyping using sequencible structures from nPCR products amplified by Pfu DNA polymerases. Nested PCR primers were designed for an SNP marker from human chromosome 6. The inner product size is 189 bp, its 3' end is positioned immediately upstream to the polymorphic site when it forms sequencible structures. PCRs were performed with DNA samples of known genotypes. After PCRs the outer and inner products were purified and denatured together to form sequencible structures. SBE reactions were performed and products analyzed in ABI 377 Sequencer using Genescan. Three samples were presented. The upper panel is a homozygous A/A where an SBE product of 190 bp is found (arrow). Products of the same size are found in the heterozygous (middle panel) and the other homozygous (lower panel). The peaks after the dye front are ROXS500 size makers (35, 50, 75, 100, 139, 150, 160, 200, 250 bp respectively).

Three samples were shown in FIG. 5, representing three genotypes for the marker: Homozygous A/A (upper panel), heterozygous A/G (middle panel) and homozygous G/G (lower panel). The experiments demonstrated that Pfu DNA polymerases produce inner PCR products with precise ends that can be used to form sequencible structures for SBE reactions and to score genotypes correctly. In a parallel experiment using Taq DNA polymerases multiple products were observed and genotypes were not clear (data not shown). The results clearly show the differences between the two DNA polymerases.

Example 3

Control of the Reading Length for Multiple Target Sequencing

The reading length of sequencing reactions is principally determined by the ratio of dNTPs/ddNTPs. For typical sequencing applications, long sequence reads are obtained by using a high dNTPs/ddNTPs ratio (~100:1) provided in commercial sequencing kits. In the practice of the present invention, a short stretch of DNA surrounding the SNP targets will be sequenced. For this purpose it is desirable to control the length of sequence reads so that multiple sequencing reactions can be loaded in one lane/capillary without overlapping each other. Currently there is no commercially available kit for this purpose, but two products, the SNaPShot from Applied Biosystems and the SNuPe from Amershan Biosciences, have the potential to be modified for this purpose. Both these kits were designed for SBE reactions, containing only dye-labeled ddNTPs. The concentration of nucleotides in the mix is proprietary.

Figure 6:
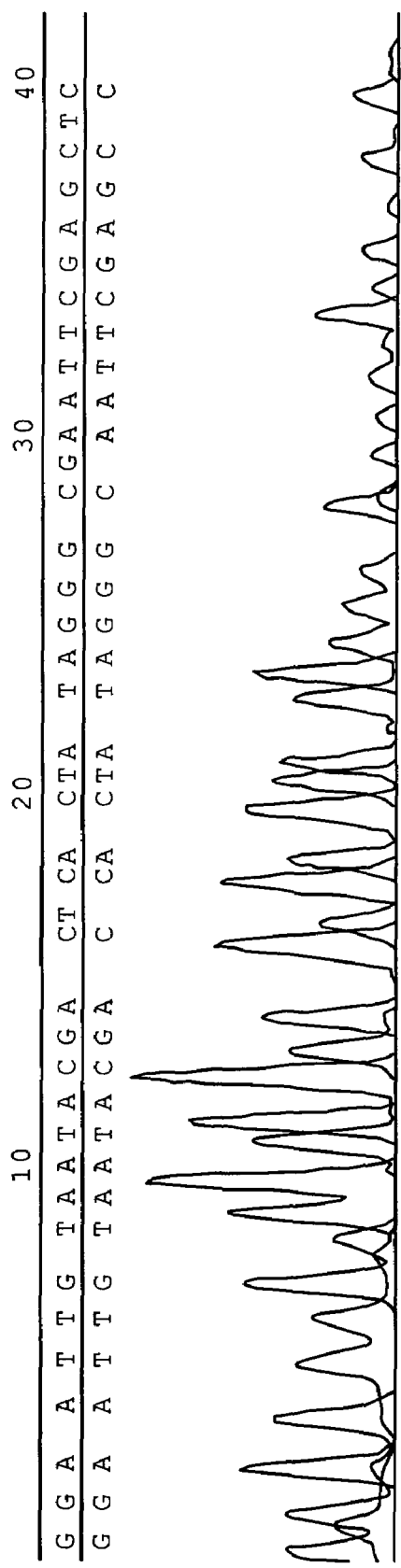
FIG. 6. An example illustrates a short sequence (SEQ ID NO: 9) read with a specially assembled sequencing mixture that has a different ddNTPs/dNTPs ratio. The components used for the example were the following: 1.75 µM of −21 M13 primer, 300 ng of pGEM, 60 µM of each dNTPs, 2.5 µM of R6G-acyclo-ATP, 12 µM of ROX-acyclo-CTP, 10 µM of BODIPY-Fluorescein-acyclo-GTP, 25 µM of TAMRA-acyclo-UTP, 1 unit of AcycloPol DNA polymerase and 1× AcycloPol reaction buffer. The thermal cycling conditions were 96° C. for 3 min., followed by 25 cycles of 96° C. for 1 min., 50° C. for 15 sec. and 60° C. for 4 min.

Individually available dye-labeled nucleotides were used to assemble a testing kit to demonstrate the principle that reading length can be controlled by dNTPs/ddNTPs ratio. FIG. 6 shows an example of the sequencing reaction. In this reaction, dye-labeled acyclo-ddNTPs were used to assemble the mix. The sequencing reaction was performed using pGEM plasmid and M13-21 primer. The ratio of dNTPs/ddNTPs and thermal cycling conditions are detailed in the figure legend. The results showed a clean read of 30-40 bases after the primer.

This example demonstrated that the reading length can be effectively controlled by the ratio of dNTPs/dDNTPs. To practice the current invention, especially the MulTarSeq, a specially formulated sequencing mix is therefore desirable.

Example 4

Comparison of Two-Step PCR Amplification Using Primary and

Secondary Primer Sets

Figure 7:
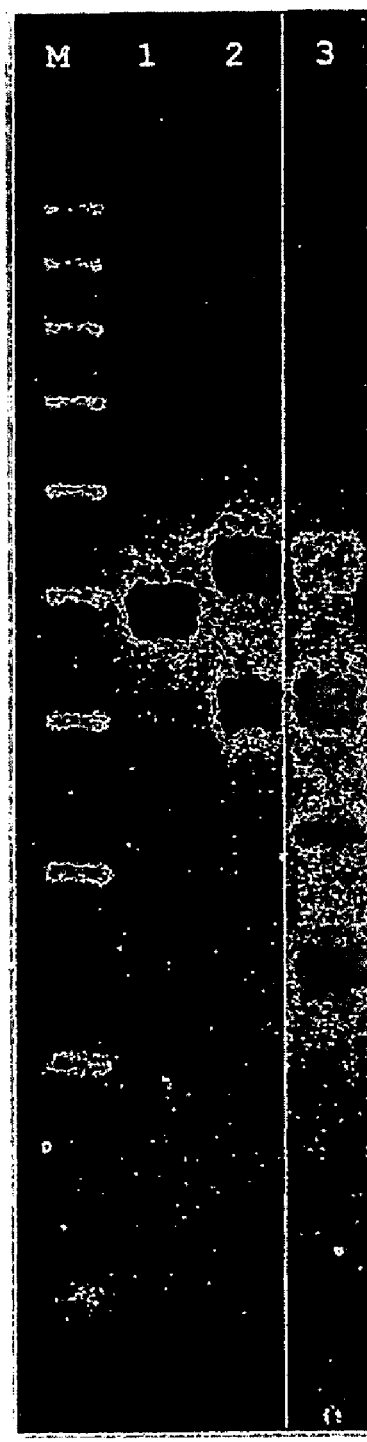
FIG. 7. Primer designs affected multiplex PCR and nPCR. Lane 1 was a 4× multiplex PCR with simple PCR design, Lane 2 was the same 4 amplicons but with the two domain design, and Lane 3 was the 4× multiplex nIPCR with the same amplicons performed in two sequential reactions. In the first reaction, equal amount of primary primers at 10 nM were used. The cycling condition was 95° C. for 10 min, followed by 10 cycles of 95° C. for 45 sec., 65° C. for 5 sec., ramping to 55° C. at 0.1° C./sec and 55° C. for 90 sec. For the second reaction the primers used were different among the three lanes. Lane 1, since it did not have secondary primers, the same primers were used as in first reaction but the concentration increased to 100 nM. Lane 2 used two secondary primers, M13 forward and reverse, each 400 nM. Lane 3 used three primers, M13 forward (600 nM), M13 reverse (400 nM) and the common tag for inner PCR primers (400 nM). The cycling conditions for the second reaction was following: 95° C. for 10 min, followed by 30 cycles of 95° C. for 45 sec., 55° C. for 90 sec.

Four SNP markers randomly were chosen from our SNP collection and PCR and nPCR primers were designed. Both outer and inner primers had two designs, a simple design and the two domain design. The sequences used for the common domains of the two domain were the M13 universal forward primer: cccagtcacgacgttgtaaaacg (SEO ID NO: 5) (for forward outer PCR primers) and M13 universal reverse primer: agcggataacaatttcacacagg (SEQ ID NO: 6) (for reverse outer PCR primers). For the inner PCR primer the common domain sequence was tcaGCAGCatGTCTCttcca, (SEQ ID NO: 7) which contains recognition sites for two restriction enzymes (Bst71I and Alw26 I, in capital letters). Multiplex PCR and multiplex nPCR reactions were performed to compare the primer designs and protocols. PCR products were then analyzed by agarose gel electrophoresis. FIG. 7 showed the results. Lane 1 of FIG. 7 represents a 4× multiplex PCR using simple primer design. As ca be seen, only two bands are visible (480,510 bp). They could not be resolved by agarose gel electrophoresis. Lane 2 represents the same 4 amplicons, but generated using the two domain design. In this case, the two smaller products (400, 430 bp) are clearly seen. Note the size shifted for the larger products due to extra length (46 bp) in the two domain primers. Lane 3 represents 4× multiplex nIPCR with the same amplicons but carried out by the two-step procedure. In addition to the 4 outer PCR products, 4 inner PCR products can also be seen. both multiplex PCR and multiplex NPCR, and that the two-step procedure is especially effective to improve multiplex nPCR.

Example 5

Use of Multiplex nPCR to Create an Ordered Series of Sequencible Structures

This example is provided to illustrate how a series of sequencible structures are formed from two multiplexed PCRS. A set of five SNPs are selected and NPCR primers are designed using the two domain design. In order to run all products on a single sequencing lane/capillary, the inner PCR products are arranged to span 150 to 400 bps range, 50 bps apart from one another. The common domain for the inner primers should contain a restriction enzyme recognition site to produce blunt ends after the amplification. Two 5× mulitiplexing PCRs are performed separately: one uses only the outer PCR primers the other uses only the inner PCR primers. After the amplification an appropriate restriction enzyme is used to remove the common tag sequences from the inner end of the inner PCR products. The outer products and the inner products then are combined, purified, denature and reannealed together. A single base extension reaction is performed using the SNaPshot kit from Applied Biosystems. The products then are purified and run on DNA sequencer. The analysis of the extension products will identify the genotypes of the sample.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Armstrong B, Stewart M, Mazumder A. 2000. Suspension arrays for high throughput, multiplexed single nucleotide polymorphism genotyping. Cytometry 40:102-8

Barta C, Ronai Z, Sasvari-Szekely M, Guttman A. 2001. Rapid single nucleotide polymorphism analysis by primer extension and capillary electrophoresis using polyvinyl pyrrolidone matrix. Electrophoresis 22:779-82

Bray M S, Boerwinkle E, Doris P A. 2001. High-throughput multiplex SNP genotyping with MALDI-TOF mass spectrometry: practice, problems and promise. Hum. Mutat. 17:296-304

Cai H, White P S, Tomey D, Deshpande A, Wang Z, Keller R A, Marrone B, Nolan J P. 2000. Flow cytometry-based minisequencing: a new platform for high-throughput single-nucleotide polymorphism scoring. Genomics 66:135-43

Chen X, Levine L, Kwok P Y. 1999. Fluorescence polarization in homogeneous nucleic acid analysis. Genome Res. 9:492-8

Chen X, Zehnbauer B, Gnirke A, Kwok P Y. 1997. Fluorescence energy transfer detection as a homogeneous DNA diagnostic method. Proc. Natl. Acad. Sci. U.S.A 94:10756-61

Chen X, Livak K J, Kwok P Y. 1998. A homogeneous, ligase-mediated DNA diagnostic test. Genome Res. 8:549-56

Chen X, Kwok P Y. 1997. Template-directed dye-teminator incorporation (TDI) assay: a homogeneous DNA diagnostic method based on fluorescence resonance energy transfer. Nucleic Acids Res. 25:347-53

Cline J, Braman J C, Hogrefe H H. 1996. PCR fidelity of pfu DNA polymerase and other thermostable DNA polymerases. Nucleic Acids Res. 24:3546-51

Coljee V W, Murray H L, Donahue W F, Jarrell K A. 2000. Seamless gene engineering using RNA- and DNA-overhang cloning. Nat. Biotechnol. 18:789-91

Collins F S, Guyer M S, Charkravarti A. 1997. Variations on a theme: cataloging human DNA sequence variation. Science 278:1580-1

Delahunty C, Ankener W, Deng Q, Eng J, Nickerson D A. 1996. Testing the feasibility of DNA typing for human identification by PCR and an oligonucleotide ligation assay. Am. J. Hum. Genet. 58:1239-46

Dubertret B, Calame M, Libchaber A J. 2001. Single-mismatch detection using gold-quenched fluorescent oligonucleotides. Nat. Biotechnol. 19:365-70

Fan J B, Chen X, Halushka M K, Berno A, Huang X, Ryder T, Lipshutz R J, Lockhart D J, Chakravarti A. 2000. Parallel genotyping of human SNPs using generic high-density oligonucleotide tag arrays. Genome Res. 10:853-60

Ferguson J A, Steemers F J, Walt D R. 2000. High-density fiber-optic DNA random microsphere array. Anal. Chem. 72:5618-24

Fors L, Lieder K W, Vavra S H, Kwiatkowski R W. 2000. Large-scale SNP scoring from unamplified genomic DNA. Pharmacogenomics. 1:219-29

Gal J, Schnell R, Szekeres S, Kalman M. 1999. Directional cloning of native PCR products with preformed sticky ends (autosticky PCR). Mol. Gen. Genet. 260:569-73

Gal J, Schnell R, Kalman M. 2000. Polymerase dependence of autosticky polymerase chain reaction. Anal. Biochem. 282:156-8

Germer S, Holland M J, Higuchi R. 2000. High-throughput SNP allele-frequency determination in pooled DNA samples by kinetic PCR. Genome Res. 10:258-66

Germer S, Higuchi R. 1999. Single-tube genotyping without oligonucleotide probes. Genome Res. 9:72-8

Gerry N P, Witowski N E, Day J, Hammer R P, Barany G, Barany F. 1999. Universal DNA microarray method for multiplex detection of low abundance point mutations. J. Mol. Biol. 292:251-62

Gilles P N, Wu D J, Foster C B, Dillon P J, Chanock S J. 1999. Single nucleotide polymorphic discrimination by an electronic dot blot assay on semiconductor microchips. Nat. Biotechnol. 17:365-70

Hu G. 1993. DNA polymerase-catalyzed addition of non-templated extra nucleotides to the 3' end of a DNA fragment. DNA Cell Biol. 12:763-70

Iannone M A, Taylor J D, Chen J, Li M S, Rivers P, Slentz-Kesler K A, Weiner M P. 2000. Multiplexed single nucleotide polymorphism genotyping by oligonucleotide ligation and flow cytometry. Cytometry 39:131-40

Kruglyak L. 1999. Prospects for whole-genome linkage disequilibrium mapping of common disease genes. Nat. Genet. 22:139-44

Kwok P Y. 2000. High-throughput genotyping assay approaches. Pharmacogenomics. 1:95-100

Lindblad-Toh K, Winchester E, Daly M J, Wang D G, Hirschhorn J N, Laviolette J P, Ardlie K, Reich D E, Robinson E, Sklar P, Shah N, Thomas D, Fan J B, Gingeras T, Warrington J, Patil N, Hudson T J, Lander E S. 2000. Large-scale discovery and genotyping of single-nucleotide polymorphisms in the mouse. Nat. Genet. 24:381-6

Lindroos K, Liljedahl U, Raitio M, Syvanen A C. 2001. Minisequencing on oligonucleotide microarrays: comparison of immobilisation chemistries. Nucleic Acids Res. 29:E69

Long A D, Langley C H. 1999. The power of association studies to detect the contribution of candidate genetic loci to variation in complex traits. Genome Res. 9:720-31

Marras S A, Kramer F R, Tyagi S. 1999. Multiplex detection of single-nucleotide variations using molecular beacons. Genet. Anal. 14:151-6

Medintz I, Wong W W, Berti L, Shiow L, Tom J, Scherer J, Sensabaugh G, Mathies R A. 2001. High-performance multiplex SNP analysis of three hemochromatosis-related mutations with capillary array electrophoresis microplates. Genome Res. 11:413-21

Metzker M L, Lu J, Gibbs R A. Electrophoretically uniform fluorescent dyes for automated DNA sequencing. Science. 1996; 271(5254): 1420-2.

Myakishev M V, Khripin Y, Hu S, Hamer D H. 2001. High-throughput SNP genotyping by allele-specific PCR with universal energy-transfer-labeled primers. Genome Res. 11:163-9

Nikiforov T T, Rendle R B, Goelet P, Rogers Y H, Kotewicz M L, Anderson S, Trainor G L, Knapp MR. 1994. Genetic Bit Analysis: a solid phase method for typing single nucleotide polymorphisms. Nucleic Acids Res. 22:4167-75

Nordstrom T, Nourizad K, Ronaghi M, Nyren P. 2000. Method enabling pyrosequencing on double-stranded DNA. Anal. Biochem. 282 :186-93

Pastinen T, Raitio M, Lindroos K, Tainola P, Peltonen L, Syvanen A C. 2000. A system for specific, high-throughput genotyping by allele-specific primer extension on microarrays. Genome Res. 10:1031-42

Pastinen T, Kurg A, Metspalu A, Peltonen L, Syvanen A C. 1997. Minisequencing: a specific tool for DNA analysis and diagnostics on oligonucleotide arrays. Genome Res. 7:606-14

Pastinen T, Partanen J, Syvanen A C. 1996. Multiplex, fluorescent, solid-phase minisequencing for efficient screening of DNA sequence variation. Clin. Chem. 42:1391-7

Perler F B, Kumar S, Kong H. 1996. Thermostable DNA polymerases. Adv. Protein Chem. 48:377-435

Prince J A, Feuk L, Howell W M, Jobs M, Emahazion T, Blennow K, Brookes A J. 2001. Robust and accurate single nucleotide polymorphism genotyping by dynamic allele-specific hybridization (DASH): design criteria and assay validation. Genome Res. 11:152-62

Riley J H, Allan C J, Lai E, Roses A. 2000. The use of single nucleotide polymorphisms in the isolation of common disease genes. Pharmacogenomics. 1:39-47

Ronaghi M. 2001. Pyrosequencing sheds light on DNA sequencing. Genome Res. 11:3-11

Ross P, Hall L, Smirnov I, Haff L. 1998. High level multiplex genotyping by MALDI-TOF mass spectrometry. Nat. Biotechnol. 16:1347-51

Sachidanandam R, Weissman D, Schmidt S C, Kakol J M, Stein L D, Marth G, Sherry S, Mullikin J C, Mortimore B J, Willey D L, Hunt S E, Cole C G, Coggill P C, Rice C M, Ning Z, Rogers J, Bentley D R, Kwok P Y, Mardis E R, Yeh R T, Schultz B, Cook L, Davenport R, Dante M, Fulton L, Hillier L, Waterston R H, McPherson J D, Gilman B, Schaffner S, Van Etten W J, Reich D, Higgins J, Daly M J, Blumenstiel B, Baldwin J, Stange-Thomann N, Zody M C, Linton L, Lander E S, Atshuler D. 2001. A map of human genome sequence variation containing 1.42 million single nucleotide polymorphisms. Nature 409:928-33

Sauer S, Lechner D, Berlin K, Plancon C, Heuermann A, Lehrach H, Gut I G. 2000. Full flexibility genotyping of single nucleotide polymorphisms by the GOOD assay. Nucleic Acids Res. 28:E100

Shi M M. 2001. Enabling large-scale pharmacogenetic studies by high-throughput mutation detection and genotyping technologies. Clin. Chem. 47:164-72

Stump M D, Cherry J L, Weiss R B. 1999. The use of modified primers to eliminate cycle sequencing artifacts. Nucleic Acids Res. 27:4642-8

Syvanen A C. 1999. From gels to chips: "minisequencing" primer extension for analysis of point mutations and single nucleotide polymorphisms. Hum. Mutat. 13:1-10

Tong J, Cao W, Barany F. 1999. Biochemical properties of a high fidelity DNA ligase from Thermus species AK16D. Nucleic Acids Res. 27:788-94

Tong J, Barany F, Cao W. 2000. Ligation reaction specificities of an NAD(+)-dependent DNA ligase from the hyperthermophile *Aquifex aeolicus*. Nucleic Acids Res. 28:1447-54

Woolley A T, Guillemette C, Li C C, Housman D E, Lieber C M. 2000. Direct haplotyping of kilobase-size DNA using carbon nanotube probes. Nat. Biotechnol. 18:760-3

Ye F, Li M S, Taylor J D, Nguyen Q, Colton H M, Casey W M, Wagner M, Weiner M P, Chen J. 2001. Fluorescent microsphere-based readout technology for multiplexed human single nucleotide polymorphism analysis and bacterial identification. Hum. Mutat. 17:305-16

---

I claim:

1. A method of producing hybrid DNA with a single strand overhang that includes a target site, comprising the steps of:

obtaining a first primer which hybridizes to a 5' strand of deoxyribonucleic acid (DNA) containing said target site, a second primer which hybridizes to a complementary strand of DNA 3' of said target site, and a third primer which hybridizes to said complementary strand of DNA 5' of said target site;

producing by nested polymerase chain reaction (PCR) using said first primer, said second primer, and said third primer, an outer amplicon which includes said target site and an inner amplicon which excludes said target site, wherein said first and second primers generate said outer amplicon and said first and third primers generate said inner amplicon; and forming at least one of a ligatable structure which includes a 3'-5' sequence which excludes said target site hybridized to a 5'-3' sequence which includes said target site and forms a single strand 3' overhang, and a sequencible structure which includes a 5'-3' sequence which excludes said target site hybridized to a 3'-5' sequence which includes said target site and forms a single strand 5' overhang.

2. The method of claim 1 wherein said target site includes at least one single nucleotide polymorphism.

3. A method of genotyping DNA of an individual by analyzing at least one target site in said DNA, comprising the steps of:

obtaining a first primer which hybridizes to a 5' strand of said DNA containing said target site, a second primer which hybridizes to a complementary strand of DNA 3' of said target site, and a third primer which hydridizes to said complementary strand of DNA 5' of said target site;

producing by nested polymerase chain reaction (PCR) using said first primer, said second primer, and said third primer, an outer amplicon which includes said target site and an inner amplicon which excludes said target site; and forming at least one of a sequencible structure which includes a 5'-3' sequence which excludes said target site hybridized to a 3'-5' sequence which includes said target site and forms a single strand 5' overhang; and a ligatable structure which includes a 3'-5' sequence which excludes said target site hybridized to a 5'-3' sequence which includes said target site and forms a single strand 3' overhang; and analyzing at least one of a sequencing product formed by sequencing said sequencible structure and a ligation product formed by ligating said ligatable structure with a labeled oligonucleotide with a DNA sequencer to determine the genotype of said individual.

4. The method of claim 3 wherein said at least one target site includes a single nucleotide polymorphism.

5. The method of claim 3 wherein said sequencible structure is sequenced by a technique selected from the group consisting of dideoxy sequencing, pyrosequencing, and single base extension.

6. The method of claim 3, wherein an ordered series of sequencible products are formed in said forming step, each being specific for a particular target site, and said sequencible products are of varying, non-overlapping lengths, and wherein said step of analyzing is carried out by electrophoresing said ordered series of sequencible products in a single channel of said DNA sequencer.

7. The method of claim 6 wherein said step of producing an ordered series of sequencing products is carried out by single base extension (SBE).

8. The method of claim 6 wherein said step of producing an ordered series of sequencing products is carried out by a dideoxy sequencing reaction utilizing a low ratio of dNTPs to ddNTPs.

9. The method of claim 3 wherein said labeled oligonucleotide is fluorescently labeled.

10. The method of claim 3 wherein a plurality of ligatable structures are formed in said forming step, each being specific for one of a plurality of target sites, and said ligation products are of varying, non-overlapping lengths with said labeled oligonucleotides being degenerate, said step of analyzing is carried out by electrophoresing a plurality of ligation products in a single channel of said DNA sequencer.

11. A method for analyzing at least one target site in a DNA molecule, comprising the steps of amplifying by nested PCR said target site, wherein said nested PCR is carried out using inner and outer PCR primer pairs, wherein said outer PCR primer pair forms a first PCR product which contains said target site, and wherein said inner PCR primer pair forms a second PCR product which contains a portion of said first PCR product but does not contain said target site,
denaturing said first and said second PCR products to form ssDNA sequences,
reannealing said ss DNA sequences to form a sequencible hybrid DNA molecule and a ligatable hybrid DNA molecule, wherein said sequencible hybrid DNA molecule includes a 5'-3' sequence which excludes said target site hybridized to a 3'-5' sequence. said 3'-5' sequence including said target site and forming a single strand 5' overhang; and wherein said ligatable hybrid DNA molecule includes a 3'-5' sequence which excludes said target site hybridized to a 5'-3' sequence, said 5'-3' sequence including said target site and forming a single strand 3' overhang, and
performing sequencing reactions with said sequencible hybrid DNA molecule and ligation reactions with said ligatable hybrid DNA molecule, and
determining the characteristics of said target site by analyzing results obtained in said performing step.

12. The method of claim 11 wherein said at least one target site is an SNP polymorphism site.

13. The method of claim 11 wherein said inner and outer primer pairs comprise a sequence tag.

14. The method of claim 13 wherein said sequence tag comprises a restriction enzyme recognition site.

15. The method of claim 13, where said step of amplifying is carried out using a low concentration of primers, and further comprising a second step of amplifying, wherein said second step of amplifying uses secondary primers for amplification of said sequence tags.

16. The method of claim 11 wherein one target site is analyzed.

17. The method of claim 11 wherein a plurality of target sites are analyzed.

18. The method of claim 11 wherein said step of amplifying is carried out in a single multiplex PCR reaction.

19. The method of claim 11 wherein said step of amplifying is carried out in multiple independent PCR reactions.

20. The method of claim 11 wherein said results obtained in said performing step are analyzed by a DNA sequencer.

* * * * *

SEQUENCE LISTING

<160> NUMBER OF SEQ ID NOS: 9

<210> SEQ ID NO 1
<211> LENGTH: 420
<212> TYPE: DNA
<213> ORGANISM: Homo sapiens

<400> SEQUENCE: 1
agtacctgtc agaatgagat taccctccag gttccaaatc cctcagaatt aagagccaag    60
ccaccttctt cttcctccac ctgcaccgac tcggccaccc gggacatcag tgagggtggg   120 gagtccccg ttgttcagtc cgatgaggag gaagttcagg tggacactgc cctggccaca   180
tcacacactg acagagaggc cactccggat ggtggtgagg acagcgactc ttaaattggg   240
acatgggcgt tgtctggcca cactggaatc cagttttggc tgtatgcgga attccacctg   300
gaaagccagg ttgtttttata gaggttcttg attttttacat aattgccaat aatgtgtgag   360
aaacttaaag aacagctaac aataaagtgt gaggacggta aactgagagc gcacagagct   420

<210> SEQ ID NO 2
<211> LENGTH: 24
<212> TYPE: DNA
<213> ORGANISM: Homo sapiens

<400> SEQUENCE: 2
tgatttttac ataattgcca ataa                                          24

<210> SEQ ID NO 3
<211> LENGTH: 540
<212> TYPE: DNA
<213> ORGANISM: Homo sapiens

<400> SEQUENCE: 3

| | | | | | |
|---|---|---|---|---|---|
| atattaggca | gtgtagcaga | tgattaagaa | catggaattc | taggtgtggt | ggctcacacc | 60 |
| tgtaatcccc | atatgtttgg | aggccaaggc | tggaggatcg | cctgagccta | ggagttagag | 120 |
| accagcctgg | gcaacagagt | gagacctcgt | ctctacaaat | aattaaaaaa | ttagctggtt | 180 |
| gtggtggtgc | atacctgtag | tccaagctcc | tccagaggct | gaggtaggag | gatcacttac | 240 |
| gtcagggagg | ttgaaggtgc | agtgagccac | gatcacatca | ctgccctcca | gcctgggcaa | 300 |
| cagagcaaga | ctctgtctct | agaaagagaa | aagaagaac  | atggaatcta | gagccagact | 360 |
| gggagtgctg | aaatgctagc | ttggatgtta | tctcacctct | ctgagcctca | gttccctctc | 420 |
| tgaaaaatga | aaatgattaa | taggacctac | atctttgaat | tgctttaaag | actgcattga | 480 |
| tacacataaa | gggtttacag | ctgtgcctgg | tatttacgta | gaagtgctgt | atataagagt | 540 |

<210> SEQ ID NO 4
<211> LENGTH: 79
<212> TYPE: DNA
<213> ORGANISM: Homo sapiens
<220> FEATURE:
<221> NAME/KEY: misc_feature
<222> LOCATION: (8)..(8)
<223> OTHER INFORMATION: unknown nucleotide
<220> FEATURE:
<221> NAME/KEY: misc_feature
<222> LOCATION: (17)..(17)
<223> OTHER INFORMATION: single nucleotide polymorphism
<220> FEATURE:
<221> NAME/KEY: misc_feature
<222> LOCATION: (38)..(38)
<223> OTHER INFORMATION: unknown nucleotide
<220> FEATURE:
<221> NAME/KEY: misc_feature
<222> LOCATION: (47)..(47)
<223> OTHER INFORMATION: unknown nucleotide
<220> FEATURE:
<221> NAME/KEY: misc_feature
<222> LOCATION: (49)..(49)
<223> OTHER INFORMATION: unknown nucleotide
<220> FEATURE:
<221> NAME/KEY: misc_feature
<222> LOCATION: (51)..(51)
<223> OTHER INFORMATION: unknown nucleotide

<400> SEQUENCE: 4

| | | | | | |
|---|---|---|---|---|---|
| acgtaagnga | tcctccnacc | tcagcctctg | gaggaggnct | tgactgnang | ngatcctccc | 60 |
| acctcagcct | ctggaggag  | | | | | 79 |

<210> SEQ ID NO 5
<211> LENGTH: 23
<212> TYPE: DNA
<213> ORGANISM: Artificial
<220> FEATURE:
<223> OTHER INFORMATION: M13 universal forward primer

<400> SEQUENCE: 5
cccagtcacg acgttgtaaa acg                                              23

<210> SEQ ID NO 6
<211> LENGTH: 23
<212> TYPE: DNA
<213> ORGANISM: Artificial
<220> FEATURE:

```
<223> OTHER INFORMATION: M13 universal reverse primer

<400> SEQUENCE: 6
agcggataac aatttcacac agg                                              23

<210> SEQ ID NO 7
<211> LENGTH: 20
<212> TYPE: DNA
<213> ORGANISM: Artificial
<220> FEATURE:
<223> OTHER INFORMATION: common domain sequence for inner PCR primer

<400> SEQUENCE: 7
tcagcagcat gtctcttcca                                                  20

<210> SEQ ID NO 8
<211> LENGTH: 23
<212> TYPE: DNA
<213> ORGANISM: Artificial
<220> FEATURE:
<223> OTHER INFORMATION: common domain of inner primer with restriction
      sites incorporated into the sequence of the domain

<400> SEQUENCE: 8
gtactggaga ctggagtcgc atg                                              23

<210> SEQ ID NO 9
<211> LENGTH: 40
<212> TYPE: DNA
<213> ORGANISM: Homo sapiens

<400> SEQUENCE: 9
ggaattgtaa tacgactcac tatagggcga attcgagctc                            40
```